United States Patent [19]

Kimoto et al.

[11] Patent Number: 5,830,914

[45] Date of Patent: Nov. 3, 1998

[54] APOPTOSIS-CONTROLLING AGENT

[75] Inventors: Tetsuo Kimoto; Hiroto Chaen; Masashi Kurimoto, all of Okayama, Japan

[73] Assignee: Kabushiki Kaisha Hayashibara Seibutsu Kagaku Kenkyujo, Okayama, Japan

[21] Appl. No.: 834,869

[22] Filed: Apr. 10, 1997

[30] Foreign Application Priority Data

Apr. 12, 1996 [JP] Japan ................................. 8-125198
Jul. 17, 1996 [JP] Japan ................................. 8-205482

[51] Int. Cl.$^6$ .................................................. A61K 31/19
[52] U.S. Cl. ............................................................ 514/510
[58] Field of Search ............................................. 514/570

[56] References Cited

U.S. PATENT DOCUMENTS 5,556,866 9/1996 Aga et al. ................................ 514/332

FOREIGN PATENT DOCUMENTS 60-163841 8/1985 Japan .
6-256177 9/1994 Japan .

OTHER PUBLICATIONS

CA 124;194307, Matsuno et al., Dec. 1995.
Zdero, C. et al., "Diterpene glycosides and other constituents from argentinian baccharis species.", Phytochemistry, vol. 25, No. 12, pp. 2841–2855 (1986).
Matsuda, Shinobu. "Propolis—Health food care.", Foods and Food Ingredients Journal of Japan, vol. 160, pp. 63–73 (1994).
Okuno, Isamu. "Studies on choleretic constituents in artemisia capillaris thunb.", Chem. Pharm. Bull., vol. 36, No. 2, pp. 769–775 (1988).
Hay, Robert et al., "Catalogue of cell lines and hydridomas.", American Type Culture Collection, 5th Ed. (1985).
Japanese Cancer Research Resources bank Newsletter, No. 9 (1989).

*Primary Examiner*—Kimberly Jordan
*Attorney, Agent, or Firm*—Browdy and Neimark

[57] ABSTRACT

An apoptosis-controlling agent comprising a carrier and as an effective ingredient 3-[4-hydroxy-3,5-bis(3-methyl-2-butenyl)phenyl]-2-propenoic acid and/or its physiologically acceptable salt(s). The agent promotes the apoptosis of abnormal cells without substantially affecting the apoptosis of normal cells.

23 Claims, 3 Drawing Sheets

Lane 1 : DNA molecular marker
Lane 2 : Compound 2 (0 μg/ml)
Lane 3 : Compound 2 (100 μg/ml)
Lane 4 : DNA molecular marker

APOPTOSIS-CONTROLLING AGENT

BACKGROUND OF THE INVENTION

1. Field of the Invention

The present invention relates to an apoptosis-controlling agent, more particularly, to an apoptosis-controlling agent comprising a carrier and 3-[4-hydroxy-3,5-bis(3-methyl-2-butenyl)phenyl]-2-propenoic acid and/or its physiologically acceptable salt(s) as an effective ingredient.

2. Description of the Prior Art

Recently, natural cell death, i.e., APOPTOSIS has been in the limelight in the field of biology. Cells in normal living bodies are programmed to naturally die after ordered generation, differentiation and ageing while replacing old cells with new ones. However, the apoptosis of abnormal cells of malignant tumors inclines to the negative direction, and the abnormal cells neither differentiate nor age independently of the original cell program but repeatedly generate without limitation until the hosts' death. In the case of AIDS, i.e., acquired immune deficiency syndrome, and Alzheimer's disease, the apoptosis of normal lymphomas and neurons in such patients inclines in the positive direction and induces immunodeficiency and dementia. Intractable and geriatric diseases may be induced by some causes which induce the apoptosis of normal and abnormal cells in a direction opposite to the normal direction. Although apoptosis-controlling substances have been required and energetically studied by investigators, no effective substance was reported. The characteristic features of apoptosis are the phenomena of cell atrophy and fragmentation observed ultramicroscopically at cell death and the phenomenon of the DNA fragmentation observed genetically. These features clearly distinguish apoptosis from other cell death.

SUMMARY OF THE INVENTION

It is an object of the present invention to provide an apoptosis-controlling agent which promotes the apoptosis of abnormal cells without substantially affecting the apoptosis of normal cells. The object is attained by an apoptosis-controlling agent comprising a carrier and 3-[4-hydroxy-3,5-bis(3-methyl-2-butenyl)phenyl]-2-propenoic acid and/or its physiologically acceptable salt(s) as an effective ingredient.

BRIEF DESCRIPTION OF THE ACCOMPANYING DRAWINGS

DETAILED DESCRIPTION OF THE INVENTION

Figure 1:
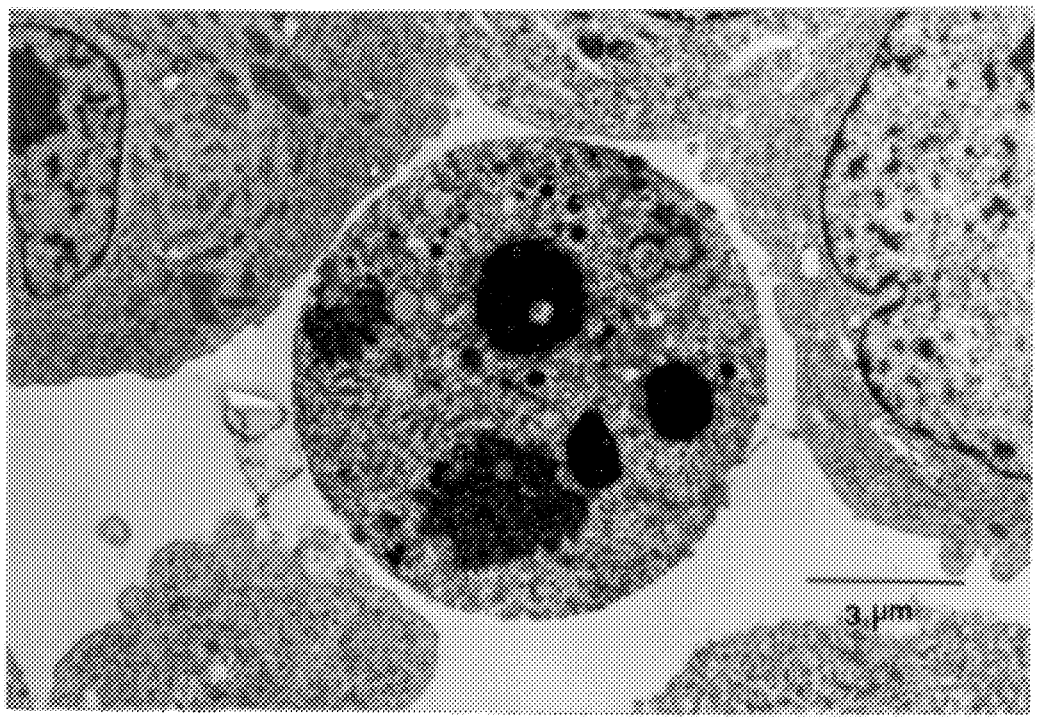
FIG. 1 is a computerized electron microscopic photograph (×7,000) of human gastric cancer cells cultured in a medium containing a salt of 3-[4-hydroxy-3,5-bis(3-methyl-2-butenyl)phenyl]-2-propenoic acid.

The present inventors energetically studied natural extracts, more particularly, the inventors studied apoptosis-controlling substances present in propolis and found 3-[4-hydroxy-3,5-bis(3-methyl-2-butenyl)phenyl]-2-propenoic acid, a derivative of cinnamic acid, or its physiologically acceptable salts have a strong apoptosis-controlling activity. Propolis has long been known to have has physiological activities such as antiseptic, anti-inflammatory and antitumor activities. Recently, propolis has been on a leading edge of the today's science technology. Sinobu Matsuda reported in "*Foods & Food Ingredients Journal of Japan*", No.160, pp.64–73 (1994) biologically active substances present in propolis extracts.

3-[4-hydroxy-3,5-bis(3-methyl-2-butenyl)phenyl]-2-propenoic acid, of which the existence and apoptosis-controlling activity were found by the present inventors, is per se a known compound. For example, the same applicant disclosed in Japanese Patent Laid-Open No.256,177/94 that the compound can be isolated from a propolis extract. As far as the inventors know, there is no publication which teaches or suggests the compound's apoptosis-controlling activity, and an apoptosis-controlling agent which comprises the compound and/or its physiologically-acceptable salt(s) is novel.

The 3-[4-hydroxy-3,5-bis(3-methyl-2-butenyl)phenyl]-2-propenoic acid and its physiologically-acceptable salts used in the present invention promote the apoptosis of abnormal cells and do not substantially affect the apoptosis of normal cells. The data of acute toxicity test using experimental animals showed that these compounds are extremely low in toxicity.

Now explaining the embodiments according to the present invention, the 3-[4-hydroxy-3,5-bis(3-methyl-2-butenyl)phenyl]-2-propenoic acid and its physiologically-acceptable salts used in the present invention have the following Chemical structure 1:

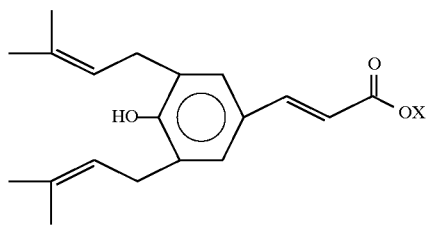

In Chemical structure 1, the symbol "X" is a physiologically-acceptable cation such as hydrogen ion, sodium ion, potassium ion, calcium ion, magnesium ion or ammonium ion.

The 3-[4-hydroxy-3,5-bis(3-methyl-2-butenyl)phenyl]-2-propenoic acid and its physiologically-acceptable salts used in the present invention are those which can be prepared from natural sources or synthesized by chemical reactions. Any one of the compounds can be used in the present invention independently of their sources as long as they have a desired apoptosis-controlling activity. Natural sources of the compounds include stems and leaves of the family Compositae such as *Artemisia capillaris Thunb*. For example, Japanese Patent Laid-Open No.256,177/94, C. Zero et al., in "*Phytochemistry*", Vol.25, No.12, pp.2,841–2, 855 (1986), and I. Okuno in "*Chemical & Pharmaceutical Bulletin*", Vol.36, No.2, pp.769–775 (1988) disclose methods for isolating 3-[4-hydroxy-3,5-bis(3-methyl-2-butenyl)phenyl]-2-propenoic acid from the above natural sources. The method disclosed in Japanese Patent Laid-Open No.163,841/85 can be advantageously used to chemically synthesize the compound.

Explaining briefly the method for isolating the compounds from natural sources, the material propolis and the stems and leaves of the family Compositae are disrupted and extracted with one or more of water and organic solvents such as methanol, ethanol, acetone, diethyl ether and ethyl acetate, followed by concentrating the extracts and purifying the concentrates. Conventional methods for concentrating and purifying compounds, which are similar to 3-[4-hydroxy-3,5-bis(3-methyl-2-butenyl)phenyl]-2-propenoic acid and the like, can be used as the concentration and purification methods for the above extracts. Examples of such methods are salting out, dialysis, filtration, concentration, separatory sedimentation, crystallization, gel filtration chromatography, ion-exchange chromatography, gas chromatography and high-performance liquid chromatography. The methods can be used alone or in combination. To obtain physiologically-acceptable salts of 3-[4-hydroxy-3,5-bis(3-methyl-2-butenyl)phenyl]-2-propenoic acid, it can be treated with hydroxides such as sodium hydroxide, potassium hydroxide, calcium hydroxide, magnesium hydroxide and ammonium hydroxide. The salts thus obtained have a higher water-solubility than the intact 3-[4-hydroxy-3,5-bis(3-methyl-2-butenyl)phenyl]-2-propenoic acid and are readily handled and processed into the desired products.

The present apoptosis-controlling agent comprises 3-[4-hydroxy-3,5-bis(3-methyl-2-butenyl)phenyl]-2-propenoic acid and/or its physiologically-acceptable salt(s) as an effective ingredient. These ingredients promote the apoptosis of abnormal cells and either inhibit the apoptosis of normal cells or do not substantially affect the apoptosis of normal cells. Therefore, the present apoptosis-controlling agent effectively treats and/or prevents diseases caused by the abnormal apoptosis of cells, promotes the recovery of health from diseases, and maintains the health when taken by or administered to humans. The wording "controlling" in "the apoptosis-controlling activity" means the action of promoting apoptosis in abnormal cells but inhibiting the abnormal apoptosis in normal cells, i.e., inducing abnormal apoptosis to normal apoptosis or inducing abnormal apoptosis to the positive direction.

The apoptosis-controlling agent according to the present invention includes those which consist of a carrier and 3-[4-hydroxy-3,5-bis(3-methyl-2-butenyl)phenyl]-2-propenoic acid and/or its physiologically-acceptable salt(s) and includes compositions, containing at least one of the above compounds, in the form of a liquid, paste or solid such as food products, cosmetics and pharmaceuticals. When the apoptosis-controlling agent is in the form of a food product, one or more of 3-[4-hydroxy-3,5-bis(3-methyl-2-butenyl)phenyl]-2-propenoic acid and its physiologically-acceptable salts can be used together with one or more of materials and ingredients which are generally used in food products such as water, alcohols, amylaceous substances, proteins, dietary fibers, saccharides, lipids, vitamins, minerals, flavors, coloring agents, sweeteners, seasonings, stabilizers and antiseptics. When the apoptosis-controlling agent is in the form of a cosmetic, one or more of 3-[4-hydroxy-3,5-bis(3-methyl-2-butenyl)phenyl]-2-propenoic acid and its physiologically-acceptable salts can be used together with one or more of main ingredients, bases, surfactants, foaming agents, humectants, viscosity-imparting agents, clearing agents, flavors, coloring agents, stabilizers, antiseptics and germicides. When the apoptosis-controlling agent is in the form of a pharmaceutical, one or more of 3-[4-hydroxy-3,5-bis(3-methyl-2-butenyl)phenyl]-2-propenoic acid and its physiologically-acceptable salts can be used together with one or more of pharmaceutically-acceptable carriers, excipients, adjuvants, diluents and stabilizers or optionally used together with one or more of other biologically active substances. All of these apoptosis-controlling agents generally contain at least 0.01% by weight of 3-[4-hydroxy-3,5-bis(3-methyl-2-butenyl)phenyl]-2-propenoic acid and/or its physiologically-acceptable salt(s). Since 3-[4-hydroxy-3,5-bis(3-methyl-2-butenyl)phenyl]-2-propenoic acid and its physiologically-acceptable salts are readily oxidized, these compounds are preferably used together with antioxidants which are generally used in food products, cosmetics and pharmaceuticals. The antioxidants are, for example, sodium nitrite, L-ascorbic acid, sodium L-ascorbate, sodium hydrogensulfite, sodium sulfite, isoquercetin, edetate calcium disodium, erythorbic acid, cysteine hydrochloride, γ-oryzanol, catechin, licorice root extract, citric acid, sodium citrate, quercetin, soybean lecithin, sodium thioglycolate, sodium thiomalate, tocotrienol, tocopherol, vitamin E, sodium pyrosulfite, potassium pyrosulfite, butylhydroxyanisole, butylhydroxytoluene, 1,3-butylene glycol, benzotriazole, gallic acid, propyl gallate, sodium metabisulfite, malic acid, rutin and enzyme-treated rutin. Usually, these antioxidants can be incorporated in the present apoptosis-controlling agent alone or in combination in an amount of about 0.01–10% by weight, preferably, in an amount of about 0.1–1% by weight of the effective ingredient(s).

The present apoptosis-controlling agent exerts a strong apoptosis-controlling activity independently of oral and parenteral administrations. Depending on use, the present agent can be orally and percutaneously administered to subjects after being shaped or processed into compositions in the form of food products or cosmetics when used to prevent diseases. When used to treat diseases, the present apoptosis-controlling agent is administered to subjects orally or parenterally in the form of injections or external applications after being shaped or processed into pharmaceutical compositions. In this case, the present apoptosis-controlling agent is administered orally or parenterally, i.e., intradermally, subcutaneously, intramuscularly or percutaneously to subjects at a dose of about one μg/shot/adult to 10 mg/shot/adult, preferably, at a dose of about 10 μg/shot/adult to one mg/shot/adult, at a rate of 1–4 shots/day or 1–5 shots/week.

The present apoptosis-controlling agent strongly treats and/or prevents diseases induced by the abnormal apoptosis of cells. Examples of such diseases are infectious diseases, immunopathies and malignant tumors which can be effectively treated and/or prevented by the intake or administration of the present agent. When used for healthy persons or patients suffering from diseases, the agent exerts a strong effect on the maintenance of health or the recovery of health from diseases.

The following experiments explain the effect and the toxicity of the present apoptosis-controlling agent:

Experiment 1

Preparation of 3-[4-hydroxy-3,5-bis(3-methyl-2-butenyl)phenyl]-2-propenoic acid and its salts Experiment 1-1

Preparation of 3-[4-hydroxy-3,5-bis(3-methyl-2-butenyl)phenyl]-2-propenoic acid

According to the method in Japanese Patent Laid-Open No.256,177/94, 3-[4-hydroxy-3,5-bis(3-methyl-2-butenyl)phenyl]-2-propenoic acid was prepared from a Brazilian propolis.

The procedure was as follows: Disrupt 153.3 parts by weight of a Brazilian propolis mass, add ethyl acetate to extract the propolis, add methanol to the resultant mixture, remove the formed sediments by centrifugation, concentrate the supernatant with an evaporator, and add ethanol to the concentrate. Remove the newly formed sediments by centrifugation, concentrate the resulting supernatant similarly as above, and add methanol to the concentrate to obtain 63.9 parts by weight of a supernatant as an extract.

Feed 35 parts by weight of the extract, on a dry solid basis (d.s.b.), to a column packed with "SILICA GEL 60G650", a silica gel commercialized by Katayama Chemical Industries, Co., Ltd., Tokyo, Japan, feed to the column a linear gradient consisting of hexane and ethyl acetate. Collect fractions eluted by the gradient with a concentration ratio of hexane to ethyl acetate, ranging from 59:41 to 57:43, pool the fractions, feed the pooled fractions to a column packed with "SEPHADEX® LH-20", an ion exchanger commercialized by Pharmacia LKB Biotechnology AB, Uppsala, Sweden, and feed methanol to the column at an SV (space velocity) 0.16. Collect fractions eluted with an eluant in an amount of about 1.1-time volumes of the packed gel, pool the fractions and concentrate the pooled fractions to effect crystallization. Wash the crystal with hexane and dry the resulting crystal to obtain 0.28 part by weight of a crystalline solid.

A portion of the crystal was analyzed using elemental analysis, mass spectrometry, ultraviolet spectroscopy, infrared spectroscopy, and nuclear magnetic resonance spectroscopy. The data were compared with the authentic ones of 3-[4-hydroxy-3,5-bis(3-methyl-2-butenyl)phenyl]-2-propenoic acid as reported by I. Okuno et al. in "*Chemical & Pharmaceutical Bulletin*", Vol.36, No.2, pp.769–775 (1988). These data well agreed and the result identified the crystal as 3-[4-hydroxy-3,5-bis(3-methyl-2-butenyl)phenyl]-2-propenoic acid (hereinafter designated as "Compound 1").

Experiment 1-2
Preparation of salts of 3-[4-hydroxy-3,5-bis(3-methyl-2-butenyl)phenyl]-2-propenoic acid The Compound 1, obtained by the method in Experiment 1-1, was dissolved in ethanol to give a concentration of about 10 w/w %, mixed with an equimolar amount of sodium hydroxide, calcium hydroxide, magnesium hydroxide or potassium hydroxide, concentrated by centrifugation, and dried to obtain a solid product of sodium salt, calcium salt, magnesium salt or potassium salt of Compound 1. Compound 1 in Experiment 1-1, sodium salt of Compound 1 (hereinafter designated as "Compound 2"), calcium salt of Compound 1 (hereinafter designated as "Compound 3"), magnesium salt of Compound 1 (hereinafter designated as "Compound 4"), or potassium salt of Compound 1 (hereinafter designated as "Compound 5") was dissolved in water to give an appropriate concentration, and the aqueous solution was sterilized in a conventional manner and filtered for the following experiments.

Experiment 2
Apoptosis-controlling activity

Experiment 2-1
Apoptosis-controlling activity in normal and abnormal cells

The apoptosis-controlling activities of Compounds 1 to 5 were ultramicroscopically checked by a system using normal cell lines and adhesive malignant tumor cell lines as human malignant tumor cell lines.

The procedure was as follows: Place MEM medium (pH 7.0) supplemented with 10 v/v % fetal calf serum in a petri dish, inoculate one of the 6 cell lines in Table 1 in the medium to give a cell density of about $1 \times 10^5$ cells/ml, and incubate the cell suspension in an incubator with 5 v/v % $CO_2$ at 37° C. for 24 hours. Suck the resultant culture by an aspirator to remove the culture supernatant, wash the cells with phosphate buffered saline (pH 7.2), add to the cells a fresh preparation of MEM medium (pH 7.0) supplemented with 10 v/v % of fetal calf serum and 0, 25, 50 or 100 μg/ml of any one of Compounds 1 to 5, and incubate the cells similarly as above.

Figure 2:
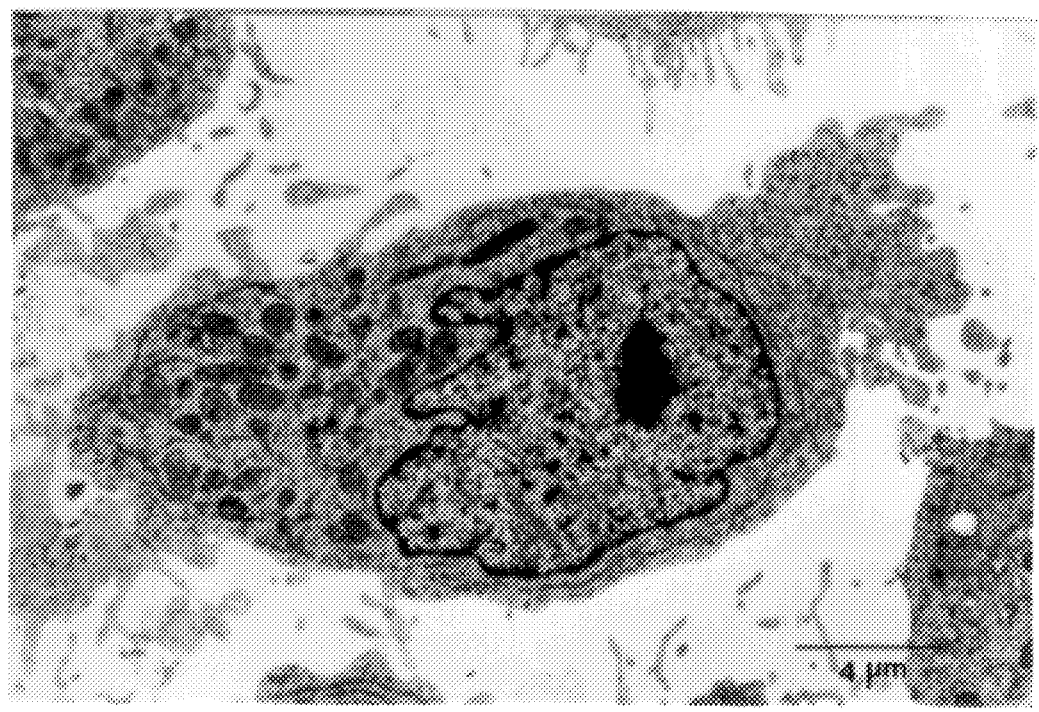
FIG. 2 is a computerized electron microscopic photograph (×5,000) of human normal skin cells cultured in a medium containing a salt of 3-[4-hydroxy-3,5-bis(3-methyl-2-butenyl)phenyl]-2-propenoic acid.

After 18 hours, treat the resultant culture with trypsin to detach the proliferated cells from the petri dish, wash the cells with physiological saline, centrifuge the cell suspension to collect the cells, treat the collected cells with 2.5 w/v % aqueous glutaraldehyde solution, and treat the cells with one w/v % aqueous osmium tetroxide solution to fix them to obtain an embedded cell specimen. Observe the specimen with a transmission electron microscope and photograph the specimen. Among the photographs, FIGS. 1 and 2 are respectively the one for HGC cells, a human gastric cell line, and the one for SF-TY cells (JCRB0075), a human normal skin cell line, both of which were cultured in media containing 100 μg/ml of Compound 2.

At the same time, the occurrence of apoptosis was observed by an electron microscope. The results were evaluated and judged as follows: Among the cells tested, the incidences of positive apoptosis of "10% or higher", "less than 10% but not less than one %" and "less than one %" were respectively expressed by the symbols "+", "±" and "−" when observing the incidence of apoptosis. The results were in Table 1. Compounds 1 to 5 were not distinctively shown in Table 1 because they did not substantially make a difference in the action on the cell lines tested.

TABLE 1

| Cell line | Origin | Occurrence of apoptosis | | | |
|---|---|---|---|---|---|
| | | 0 μg/ml | 25 μg/ml | 50 μg/ml | 100 μg/ml |
| HGC | Human gastric cancer (abnormal cell) | − | + | + | + |
| HLC | Human lung cancer (abnormal cell) | − | ± | + | + |
| PLC/PRF/5 (ATCC CRL 8024) | Human hepatoma (abnormal cell) | − | − | ± | + |
| RPMI 4788 (FERM BP-2429) | Human colon caner (abnormal cell) | − | ± | + | + |
| CCD-14Br (ATCC CCL 203) | Human bronchiole (normal cell) | − | − | − | − |
| SF-TY (JCRB0075) | Human skin (normal cell) | − | − | − | − |

The results in Table 1 and FIG. 1 showed that Compounds 1 to 5 acted on tumor cells, i.e., human abnormal cells, and positively promoted their apoptosis. Electron microscopic observation revealed that in FIG. 1, an ultramicroscopic photograph for human abnormal cells cultured in the presence of any one of Compounds 1 to 5, the center cell more highly caused the cell atrophy than usual, and the nucleus, a black site, was fragmented and dispersed in the cell. These phenomena specific to apoptosis were more apparent in this order in HGC cells, a human gastric cancer cell line, RPMI 4788 cells (FERM BP-2429), a human colon cancer cell line, HLC cells, a human lung cancer cell line, and PLC/PRF/5 cells, a human hepatoma cell line. As is apparent from the results in Table 1 and FIG. 2, the normal cells, even if treated with the compounds similarly as were the abnormal cells, did not show such phenomena. These facts show that 3-[4-hydroxy-3,5-bis(3-methyl-2-butenyl)phenyl]-2-propenoic acid and its physiologically acceptable salts promote the apoptosis of abnormal cells in human bodies but do not substantially affect the apoptosis of normal cells in the bodies.

Experiment 2-2

Apoptosis-controlling activity on abnormal cells

Compounds 1 to 5, prepared by the method in Experiment 1, were tested to check their apoptosis-controlling activities through their DNAs on a system using U-937 cells (ATCC CRL 1593) and HL-60 cells (ATCC CCL 240), both of which are human abnormal leukocyte cell lines.

The procedure was as follows: Place RPMI 1640 medium (pH 7.0), supplemented with 10 v/v % fetal calf serum, in a culture bottle, inoculate one of the 2 human abnormal cell lines in Table 2 to give a cell density of about $4 \times 10^5$ cells/ml, add to the culture 0, 25, 50 or 100 µg/ml of any one of Compounds 1 to 5 prepared by the method in Experiment 1, and incubate the cells in a 5 v/v % $CO_2$ incubator at 37° C. for 7 or 24 hours.

The cells were collected from the culture by centrifugation and washed with phosphate buffered saline. A portion of the cells was treated similarly as in Experiment 2-1 to obtain an embedded cell specimen which was then observed with an electron microscope and photographed. Another portion of the resting cells was placed in a container, treated with "Easy-DNA™ KIT", a genomic DNA isolation kit commercialized by Invitrogen BV, NV Leek, Netherlands, to extract DNAs, followed by electrophoresing the DNAs along with DNA molecular markers of 100 base-pair ladders in 1.5 w/v % agarose gel in a conventional manner, transferring the gel onto a UV transilluminator and photographing the gel.

Figure 3:
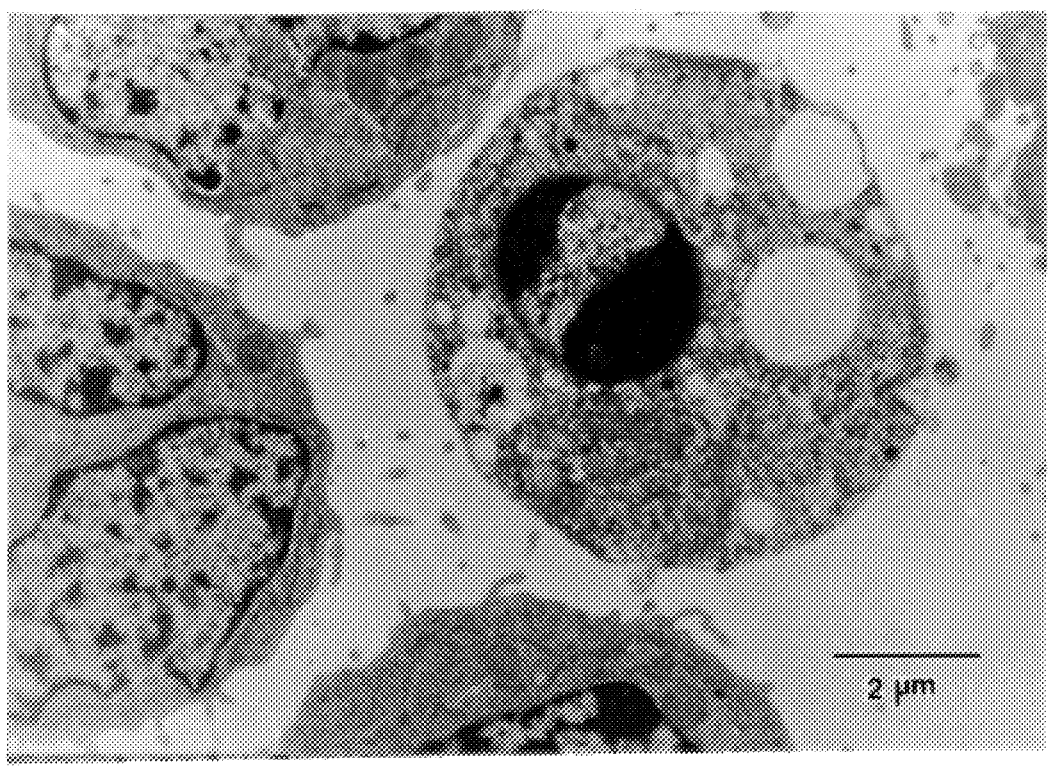
FIG. 3 is a computerized electron microscopic photograph (×10,000) of human leukemia cells cultured in a medium containing a salt of 3-[4-hydroxy-3,5-bis(3-methyl-2-butenyl)phenyl]-2-propenoic acid.
Figure 4:
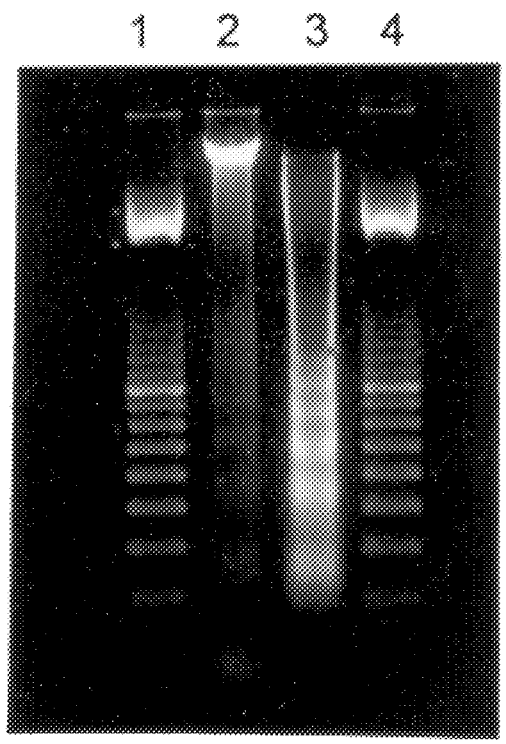
FIG. 4 is a computerized photograph of a gel electrophoresis pattern of an agarose gel electrophoresis of DNAs prepared by culturing human leukemia cells in a medium containing a salt of 3-[4-hydroxy-3,5-bis(3-methyl-2-butenyl)phenyl]-2-propenoic acid and extracting the DNAs from the cells.

Thereafter, the photographed gel electrophoresis pattern was analyzed and evaluated as follows: When the DNA fragmentation, i.e., "ladders", specific to apoptosis was found, it was expressed with the symbol "+", while the DNA fragmentation was not found it was expressed with the symbol "−". The results were in Table 2. Compounds 1 to 5 were not distinctively shown in Table 2 because they did not substantially act distinctively on the cell lines tested. FIG. 3 is an ultra-microscopic photograph of U-937 cells (ATCC CRL 1593) cultured for 24 hours in a culture medium containing 100 µg/ml Compound 2, and FIG. 4 is a photograph of an gel electrophoresis pattern of the DNAs extracted from the U-937 cells (ATCC CRL 1593).

TABLE 2

| Human leukocyte cell line | Culture time (hour) | Compounds 1 to 5 (µg/ml) | Formation of ladder |
|---|---|---|---|
| U-937 (ATCC CRL 1593) | 7 | 0 | − |
| | | 23 | − |
| | | 50 | − |
| | | 100 | + |
| | 24 | 0 | − |
| | | 25 | − |
| | | 50 | + |
| | | 100 | + |
| HL-60 (ATCC CCL 240) | 7 | 0 | − |
| | | 25 | − |
| | | 50 | − |
| | | 100 | + |
| | 24 | 0 | − |
| | | 25 | − |
| | | 50 | − |
| | | 100 | + |

As is evident from FIG. 3, similarly as in the case of adherent tumor cells used in Experiment 2-1, the non-adherent tumor cells in Experiment 2-2 shrank more than usual, and the nucleus in the cell, positioned in the right site near to the center of the photograph, nearly broke. As is shown in FIG. 4, i.e., a gel electrophoresis pattern, ladders were clearly found in the DNAs extracted from the non-adherent cells. As is apparent from the results in Table 2, the ladders dependently formed on the concentration of Compounds 1 to 5 and the culture time. The data indicates that the cell atrophy and the nucleus fragmentation observed ultramicroscopically were caused by apoptosis.

Experiment 3

Acute toxicity test

Mice in a group consisting of 10 ddy-mice, 10–20 g by weight, were intraperitoneally injected with or orally administered using a sound for stomach with a physiological saline containing 5 w/w % arabic gum and an adequate amount of any one of Compounds 1 to 5, obtained by the method in Experiments 1-1 and 1-2. Thereafter, the mice were observed for 7 days to check the number of dead mice. The $LD_{50}$ of each compound was determined by the Van der Waerden's method. As a result, the $LD_{50}$ of Compounds 1 to 5 was 200 mg/kg mouse or higher independently of their administration routes. Considering that 3-[4-hydroxy-3,5-bis(3-methyl-2-butenyl)phenyl]-2-propenoic acid and its physiologically acceptable salts are generally effective at a dose of at least several µg/shot/adult, the data of $LD_{50}$ would evidence the safeness of the present apoptosis-controlling agent containing one or more of the compounds as an effective ingredient.

The following examples are the preferred embodiments according to the present invention in detail:

Example 1

Health food

One hundred and fifty parts by weight of "MABIT®", a hydrogenated maltose syrup commercialized by Hayashibara Shoji, Inc., Okayama, Japan, were concentrated by heating under a reduced pressure up to give a water content of 15 w/w %, and the concentrate was mixed to homogeneity with 13 parts by weight of gelatin dissolved in 18 parts by weight of water, 0.05 part by weight of any one of Compounds 1 to 5 obtained by the method in Experiment 1, one part by weight of citric acid, one part by weight of L-ascorbic acid, and adequate amounts of a coloring agent and a flavor. The mixture was shaped and packed to obtain 5 types of gummy candies containing one of Compounds 1 to 5.

Since the apoptosis-controlling activities of the products are not substantially reduced because the products contain antioxidants, and the products have a satisfactory texture, flavor and taste, they can be arbitrarily used as health foods.

Example 2

Health food

Three parts by weight of gum base was dissolved by heating until it softened, mixed with 4 parts by weight of sucrose and 3 parts by weight of maltose powder, 0.001 part by weight of any one of Compounds 1 to 5 obtained by the method in Experiment 1, 0.1 part by weight of vitamin E, and an adequate amount of a coloring agent. The mixture was kneaded in a conventional manner, shaped and packed to obtain 5 types of chewing gums containing one of Compounds 1 to 5.

Since the apoptosis-controlling activities of the products are not substantially reduced because the products contain an antioxidant, and the products have a satisfactory texture, flavor and taste, they can be arbitrarily used as health foods.

Example 3

Beverage as health food

Ten parts by weight of skim milk was sterilized by heating at 80° C. for 20 min, cooled to 40° C. and admixed with 0.3 part by weight of a starter, followed by the fermentation at about 37° C. for 10 hours. The fermented product was homogenized, mixed with 5 parts by weight of isomaltooligosaccharide syrup, one part by weight of sucrose, and 2 parts by weight of isomerized syrup, and the mixture was sterilized by heating at 70° C. Thereafter, the mixture was cooled, then mixed with 0.01 part by weight of any one of Compounds 1 to 5 obtained by the method in Experiment 1, and 0.01 part by weight of malic acid, and bottled to obtain 5 types of lactic acid beverages containing one of Compounds 1 to 5.

Since the apoptosis-controlling activities of the products are not substantially reduced because the products contain an antioxidant, and the products have a satisfactory texture, flavor and taste, they can be arbitrarily used as health beverages.

Example 4

Cosmetic

A half part by weight of polyoxyethylene behenyl ether, one part by weight of polyoxyethylene sorbitol tetraoleate, one part by weight of glyceryl monostearate, lipophilic, 0.5 part by weight of pyruvic acid, 0.5 part by weight of behenyl alcohol, one part by weight of avocado oil, 0.05 part by weight of any one of Compounds 1 to 5 obtained by the method in Experiment 1, and adequate amounts of vitamin E and an antiseptic were dissolved by heating in a conventional manner. The solution was admixed with one part by weight of sodium L-lactate, 5 parts by weight of 1,3-butylene glycol, 0.1 part by weight of carboxy vinyl polymer, and 85.3 parts by weight of refined water, and the resulting mixture was emulsified by a homogenizer and mixed to homogeneity with an adequate amount of a flavor to obtain 5 types of milky lotions containing one of Compounds 1 to 5.

Since the apoptosis-controlling activities of the products are not substantially reduced because the products contain antioxidants, and the products have a satisfactory texture, flavor and taste, they can be arbitrarily used as cosmetics.

Example 5

Tablet

Ten parts by weight of L-ascorbic acid were mixed to homogeneity with 0.5 part by weight of any one of Compounds 1 to 5 obtained by the method in Experiment 1, 19 parts by weight of crystalline α-maltose powder, and one part by weight of "αG RUTIN", α-glycosyl rutin commercialized by Toyo Sugar Refining Co., Ltd., Tokyo, Japan. The mixture was tabletted in a conventional manner to obtain 5 types of tablets containing one of Compounds 1 to 5.

Since the apoptosis-controlling activities of the tablets are substantially not reduced because the tablets contain an antioxidant, and the tablets are readily swallowable and satisfactorily stable, they can be arbitrarily used to treat and/or prevent diseases, recover health from diseases, and maintain health.

Example 6

Liquid

In 1,000 parts by weight of 2 v/v % aqueous ethanol solution were dissolved 6 parts by weight of sodium chloride, 0.3 part by weight of potassium chloride, 0.2 part by weight of calcium chloride, 3.1 parts by weight of sodium lactate, 45 parts by weight of maltose, 0.005 part by weight of any one of Compounds 1 to 5 obtained by the method in Experiment 1, and 0.5 part by weight of L-ascorbic acid. The solution was membrane filtered in a conventional manner, and 25 ml aliquots of the solution were injected into sterilized plastic vessels to obtain 5 types of liquids containing one of Compounds 1 to 5.

Since the apoptosis-controlling activities of the liquids are not substantially reduced because the liquids contain an antioxidant, and the liquids satisfactorily supplement energy and minerals to living bodies, they can be arbitrarily used as injections for promoting the treatment of diseases and recovering the health from diseases.

As is described above, the present invention was made based on the unique finding that 3-[4-hydroxy-3,5-bis(3-methyl-2-butenyl)phenyl]-2-propenoic acid and its physiologically acceptable salts exert a significant apoptosis-controlling activity in humans. Since these compounds are of natural origin or present in the natural world, they are safer than artificially synthesized compounds. Therefore, the present apoptosis-controlling agent comprising a carrier and one or more of the compounds as an effective ingredient has a benefit that it can be habitually used without fear of causing side effects in the form of food products, cosmetics or pharmaceuticals which treat and/or prevent human diseases, recover health from diseases, and maintain health. Furthermore, the present agent, which optionally contains an antioxidant(s), has a relatively-long shelf life because the antioxidant(s) well stabilizes the apoptosis-controlling activity of the effective ingredient(s).

While there has been described what is at present considered to be the preferred embodiments of the invention, it will be understood the various modifications may be made therein, and it is intended to cover in the appended claims all such modifications as fall within the true spirit and scope of the invention.

We claim:

1. An orally and parenterally administrable apoptosis-controlling agent comprising an orally and parenterally administrable carrier, an antioxidant, and as an effective ingredient at least one member selected from the group consisting of 3-[4-hydroxy-3,5-bis(3-methyl-2-butenyl) phenyl]-2-propenoic acid and its physiologically acceptable salts, wherein the antioxidant is present in an amount of 0.1–10% by weight of the effective ingredient.

2. An apoptosis-controlling agent according to claim 1 wherein said physiologically acceptable salt is selected from the group consisting of sodium salt, potassium salt, calcium salt, magnesium salt, and ammonium salt of 3-[4-hydroxy-3,5-bis(3-methyl-2-butenyl)phenyl]-2-propenoic acid.

3. An apoptosis-controlling agent according to claim 1 wherein said 3-[4-hydroxy-3,5-bis(3-methyl-2-butenyl)phenyl]-2-propenoic acid and said physiologically acceptable salts thereof are derived from propolis.

4. An apoptosis-controlling agent according to claim 1 wherein said 3-[4-hydroxy-3,5-bis(3-methyl-2-butenyl)phenyl]-2-propenoic acid and said physiologically acceptable salts thereof are present in an amount of at least 0.01% by weight.

5. An apoptosis-controlling agent according to claim 1 wherein said orally and parenterally administrable carrier is selected from the group consisting of foods, cosmetics, and pharmaceuticals.

6. An apoptosis-controlling agent according to claim 1 which is directed to treating abnormal cells.

7. A method for controlling apoptosis comprising administering to a patient in need thereof an apoptosis-controlling agent comprising a carrier and as an effective ingredient at least one member selected from the group consisting of 3-[4-hydroxy-3,5-bis(3-methyl-2-butenyl)phenyl]-2-propenoic acid and its physiologically acceptable salts.

8. A method according to claim 7 wherein said physiologically acceptable salt is selected from the group consisting of sodium salt, potassium salt, calcium salt, magnesium salt, and ammonium salt of 3-[4-hydroxy-3,5-bis(3-methyl-2-butenyl)phenyl]-2-propenoic acid.

9. A method according to claim 7 wherein said 3-[4-hydroxy-3,5-bis(3-methyl-2-butenyl)phenyl]-2-propenoic acid and said physiologically acceptable salts thereof are derived from propolis.

10. A method according to claim 7 wherein said 3-[4-hydroxy-3,5-bis(3-methyl-2-butenyl)phenyl]-2-propenoic acid and its physiologically acceptable salts are present in an amount of at least 0.1% by weight.

11. A method according to claim 7 wherein said orally and parenterally administrable carrier is selected from the group consisting of foods, cosmetics, and pharmaceuticals.

12. A method according to claim 7 wherein said patient is suffering from abnormal cells.

13. A method according to claim 7 wherein said agent is administered to the patient at a dose of one $\mu$g/shot/adult to 10 mg/shot/adult and at a rate of 1–4 shots/day.

14. A method according to claim 7 wherein said agent is administered to the patient at a dose of one $\mu$g/shot/adult to 10 mg/shot/adult and at a rate of 1–5 shots/week.

15. A method for controlling apoptosis comprising administering to a patient in need thereof an apoptosis-controlling agent comprising a carrier, an antioxidant, and as an effective ingredient at least one member selected from the group consisting of 3-[4-hydroxy-3,5-bis(3-methyl-2-butenyl)phenyl]-2-propenoic acid and its physiologically acceptable salts.

16. A method according to claim 15 wherein said antioxidant is present in an amount of from 0.01–10% by weight of the effective ingredient.

17. A method according to claim 15 wherein said physiologically acceptable salt is selected from the group consisting of sodium salt, potassium salt, calcium salt, magnesium salt, and ammonium salt of 3-[4-hydroxy-3,5-bis(3-methyl-2-butenyl)phenyl]-2-propenoic acid.

18. A method according to claim 15 wherein said 3-[4-hydroxy-3,5-bis(3-methyl-2-butenyl)phenyl]-2-propenoic acid and said physiologically acceptable salts thereof are derived from propolis.

19. A method according to claim 15 wherein said 3-[4-hydroxy-3,5-bis(3-methyl-2-butenyl)phenyl]-2-propenoic acid and said physiologically acceptable salts thereof are present in an amount of at least 0.01% by weight.

20. A method according to claim 15 wherein said carrier is selected from the group consisting of foods, cosmetics, and pharmaceuticals.

21. A method according to claim 15 wherein said patient is suffering from abnormal cells.

22. A method according to claim 15 wherein said agent is administered to the patient at a dose of one $\mu$g/shot/adult to 10 mg/shot/adult and at a rate of 1–4 shots/day.

23. A method according to claim 15 wherein said agent is administered to the patient at a dose of one $\mu$g/shot/adult to 10 mg/shot/adult and at a rate of 1–5 shots/week.

\* \* \* \* \*